US005942659A

United States Patent [19]
Alibert et al.

[11] Patent Number: 5,942,659
[45] Date of Patent: Aug. 24, 1999

[54] PROCESS FOR PRODUCING FATTY ACIDS OR DERIVATIVES THEREOF FROM OLEAGINOUS PLANTS

[75] Inventors: Gilbert Alibert, Castanet; Zéphirin Mouloungui, Toulouse; Alain Boudet, Toulouse, all of France

[73] Assignee: Institut National Polytechnique de Toulouse (I.N.P.T.), Toulouse, France

[21] Appl. No.: 08/776,210

[22] PCT Filed: Jul. 18, 1995

[86] PCT No.: PCT/FR95/00957

§ 371 Date: Jan. 24, 1997

§ 102(e) Date: Jan. 24, 1997

[87] PCT Pub. No.: WO96/03511

PCT Pub. Date: Feb. 8, 1996

[30] Foreign Application Priority Data

Jul. 25, 1994 [FR] France ................................... 94.09272

[51] Int. Cl.$^6$ .............................. C12N 5/14; C12N 15/52; A01H 5/00
[52] U.S. Cl. .......................... 800/281; 800/287; 800/288; 800/295; 800/298
[58] Field of Search ..................................... 800/205, 250, 800/281, 287, 288, 295, 298; 435/69.1, 172.3, 320.1

[56] References Cited

FOREIGN PATENT DOCUMENTS

| 0 427 309 | 5/1991 | European Pat. Off. . |
| 0 449 376 | 10/1991 | European Pat. Off. . |
| WO 91/06661 | 5/1991 | WIPO . |
| WO 92/01042 | 1/1992 | WIPO . |
| WO 92/05249 | 4/1992 | WIPO . |
| WO 93/03161 | 2/1993 | WIPO . |

OTHER PUBLICATIONS

K. J. Harrington et al., "Transesterification in Situ of Sunflower Seed Oil", American Chemical Society, 1985.24, pp. 314–318.

G. P. McNeill et al., "High–Yield Enzymatic Glycerolysis of Fats and Oils", JAOCS, Jan., 1991, vol. 68, No. 1, pp.1–5.

S. M. Kim et al., "Production of Medium–Chain Glycerides by Immobilized Lipase in a Solvent–Free Systems", JAOCS, Jul. 1991., vol. 68, No. 7, pp. 499–503.

R. Arrhizus, "Catalysis with Immobilized Enzymes: Hydrolysis and Esterification", M. Guisnet et al. (Editors), Heterogeneous Catalysis and Fine Chemicals II, 1991, Elsevier Science Publishers, B.V., Amsterdam, pp. 92–105.

P. J. J. Hooykaas et al., "The Ti–plasmid of Agrobacterium tumefaciens: a natural genetic engineer", TIBS Dutch Biochemistry, Aug. 1985, pp. 307–309.

J. A. Russell, et al., "Major Improvements in Biolistic Transformation of Suspension–Cultured Tobacco Cells", In Viro Cell. Dev. Biol. 28P:97–105, Apr. 1992, Tissue Culture Association 1054–5476/92, pp. 97–No. 5.

A. Crossway et al., "Integration of foreign DNA following microinjection of tobacco mesophyll protoplasts", MGG Springer Verlag 1986, Mel Gen. Genet, vol. 202, pp. 179–185.

B. Huang et al., Effects of culture density, conditioned medium and feeder cultures on microspore embryogenesis in Brassica napus L. cv. Topas , Plant Cell Reports, Springer Verlag 1990, vol. 8, pp. 594–597.

M. F. Jardinaud, et al., "Transient GUS gene expression in Brassica napus electroporated microspores", Plant Science 93, 1993, pp. 177–184.

K. Stalberg, et al., "Deletion analysis of a 2S seed storage protein promoter of Brassica napus in transgenic tobacco", Plant Molecular Biology, 1993, vol. 23, pp. 671–683, 1993 Kluwer Academic Publishers, Printed in Belgium.

W. Kugimiya, et al., "Cloning and Sequence Analysis of cDNA encoding Rhizopus niveus Lipase", Biosci. Biotech. Biochem., 1992, 56 (5), pp. 716–719.

J. L. Brewbaker, et al., "The Essential Role of Calcuim Ion In Pollen Germination and Pollen Tube Growth", American Journal of Botany, vol. 50, No. 9, Oct. 1963, pp. 859–865.

O. L. Gamborg et al., "Nutrient Requirements of Suspension Cultures of Soybean Root Cells", Experimental Cell Research, 50, 1868, by Academic Press Inc., pp. 151–158.

J. Pen et al., "Production of Active Bacillus Licheniformis Alpha–Amylase in Tobacco and its Application in Starch Liquefaction", *BIOTECHNOLOGY*, vol. 10, No. 3, Mar. 1992, New York , pp. 292–296.

J. Pen et al., "Production of Active Alpha–Amylase in Plants and the Application in Starch Liquefaction", *Journal of Cellular Biochemistry Supplement*, vol. 16F, 1992, p. 227.

Jervis et al., Journal of Biotechnology 11:161–198, 1989.

*Primary Examiner*—Elizabeth Kemmerer
*Attorney, Agent, or Firm*—Young & Thompson

[57] ABSTRACT

A process for producing fatty acids or fatty acid derivatives from oleaginous plants. This process is characterized in that transgenic oleaginous plants are produced having on the one hand at least one gene coding for a lipase enzyme, the so-called lipase gene, and on the other hand, associated with this lipase gene, a promoter permitting an expression of the gene either in compartments different from the lipid accumulation compartments, or by exogenous induction. The seeds or fruits containing the plant lipids are collected, the seeds or fruits are crushed, if necessary after induction treatment, so as to bring the lipids and lipase into contact, the whole mixture is incubated in order to effect an enzymatic hydrolysis of the lipids, and the fatty acids or derivatives thereof are extracted.

18 Claims, 1 Drawing Sheet

FIG. 1

PROCESS FOR PRODUCING FATTY ACIDS OR DERIVATIVES THEREOF FROM OLEAGINOUS PLANTS

CROSS-REFERENCE TO RELATED APPLICATIONS

This application is the 35 USC §371 National phase of International application PCT/FR95/00957 filed Jul. 18, 1995, which designated the United States of America.

FIELD OF THE INVENTION

The invention relates to a process for producing fatty acids or derivatives of fatty acids (esters or other derivatives) from oleaginous plants. The process of the invention applies in particular to oleoproteaginous plants such as rapeseed, sunflower, soya, kale, etc. The invention may in particular be used to produce biofuels (diesters), lubricants, phytosanitary adjuvants, detergents, etc., by converting the resultant fatty acids.

BACKGROUND OF THE INVENTION

Since 1970 numerous attempts have been made to replace products derived from petroleum (in particular fuels) by products obtained from vegetable matter so as to reduce the dependency on oil-producing countries and increase the markets and sales of agricultural products. The industrial route utilizing oleaginous plants as starting materials starts from the production of free fatty acids constituting the raw materials for the conversion industries and ends up with fuels, lubricants, etc. The lipids accumulated by the oleaginous plants may be converted into fatty acids by hydrolysis: two processes are currently used industrially to effect this conversion.

The first process consists in hydrolyzing the lipids after extraction by contacting the extracted lipids under conditions of heat and pressure with sulphuric acid/methanol or methanolic potassium hydroxide. Another process consists in carrying out the hydrolysis under similar conditions directly on the crushed seed material without prior extraction. Further details of these processes, which are the only ones used industrially to hydrolyze vegetable oils, may be found in the following reference: K. J. Harrington and C. d'Arcy-Evans, Ind. Eng. Chem. Prod. Res. Dev. 1985, 24, 314–318. The well-known high operating costs, large industrial infrastructure, polluting nature of the effluents, production of glycerol as a by-product without an existing market. These processes are used on account of the lack of simple alternatives.

In addition, experiments have been carried out in the laboratory to effect the hydrolysis of lipids enzymatically by mixing a lipase with the lipids extracted from seeds (G. P. McNeill et al., JAOCS, Vol. 68 No. 1st January 1991, p. 1–5; S. M. Kim and J. S. Rhee, JAOCS Vo. 68 No. 7th July 1991, p. 499–503; C. Gancet, In Heterogeneous Catalysis And Fine Chemicals II 1991, Guisnet Editors, p. 93–104). However, these experiments have remained at the laboratory stage since the technique is incompatible with an industrial exploitation on account of the amounts of enzyme required and the cost of the latter.

It should be emphasized that processes are already known enabling enzymes to be produced from plants (patent WO-A-92/01042 and EP-A-0.449.376). These processes lead to the linexpensive production of enzymes which are then used, after or without having been isolated, in various industrial or food industry conversion processes.

Nevertheless, this teaching is completely unconnected with the problem in question, which concerns the production of fatty acids directly from oleaginous plants.

OBJECTS OF THE INVENTION

The present invention aims to provide a new solution to the problem of producing fatty acids from oleaginous plants. The invention seeks to provide a solution whose costs of implementation are considerably less than known processes (industrial chemical processes as well as laboratory enzymatic processes).

An object of the invention is thus to provide a process that can be carried out on an industrial scale under mild temperature and pressure conditions, which is simple to operate and is non-polluting, employs a small-scale infrastructure, and does not produce any harmful by-product.

Another object, associated with the previous one, is to enable the number of fatty acid production installations to be increased so that they can be sited close to the regions of cultivation of the oleaginous plants and thereby achieve savings in transportation of raw materials.

SUMMARY OF THE INVENTION

To this end, the process according to the invention for producing fatty acids or fatty acid derivatives from oleaginous plants is characterized in that:

oleaginous plants are produced transgenic oleaginous plants are produced having, on the one hand, at least one gene coding for a lipase enzyme, the so-called lipase gene, and on the other hand, associated with this lipase gene, a promoter permitting an expression of the gene either in cellular, extracellular or tissue compartments other than those in which the plant lipids accumulate, or permitting exogenous induction, the seeds or fruits containing the lipids of the plants are collected, the seeds or fruits are crushed, if necessary after induction treatment, so as to bring into mutual contact the lipids and lipase contained in the seeds or fruits, p1 the mixture is allowed to incubate to effect an enzymatic hydrolysis of the lipids of the ground material under the catalytic action of the lipase contained in the said crushed material, the fatty acids formed by the hydrolysis are extracted or are converted in order to obtain the desired fatty acid derivatives.

The process of the invention is thus an enzymatic hydrolysis process that enjoys the advantages of this type of process (mild operating conditions, absence of pollution, small-scale and inexpensive installations, no harmful by-products). In this process the plant itself is induced to produce the enzyme necessary for the subsequent transformation of the lipids, this enzyme being prevented from coming into contact prematurely with the lipids so as to avoid any risk of self-degradation of the plant before harvesting. The hydrolysis then takes place without the addition of exogenous enzyme by bringing the lipids and enzymes produced by the plant into contact. Such a process has a particularly low overall operating cost. The crushing and incubating units are light and small-scale and are known in the agricultural industry, which means that these operations can be carried out at the sites where the plants are harvested.

The production of the transgenic plants is carried out by first of all effecting the genetic transformation of a natural oleaginous plant, causing the genetically transformed plant to reproduce sexually so as to produce transgenic seeds, and then using these seeds to obtain transgenic plant progeny.

The initial genetic transformation consists, according to a presently well-known process, of generating an expression cassette containing the lipase gene and the expression promoter of this gene and introducing this expression cassette into the genome of the plant.

One of the essential characteristics of the process of the invention is that the promoter associated with the lipase gene is adapted to prevent any premature contact of the enzyme and lipids; this promoter may be of various types: it may either (1) direct the expression of the gene in compartments other than those where the lipids accumulate, or (2) initiate the expression of the gene at a suitable moment by exogenous induction.

In the first case, two types of expression cassettes may be used:

(1A) either an expression cassette comprising a lipase gene and a promoter controlling the expression of this gene in a cellular or tissue compartment different from the lipid accumulation compartment, (1B) or an expression cassette comprising a constituent promoter and a lipase gene provided with an address sequence for cellular or extracellular compartments other than those where the lipids accumulate.

In the second case (2) the promoter used in the expression cassette is of a type that can be controlled in an exogenous manner by physical, chemical or biochemical signals, in particular is a stress promoter controlling the expression by applying a physical shock to the seeds or fruits.

By way of example, to produce fatty acids from oleoproteaginous plants, the operating procedure 1A outlined above may be employed:

the genetic transformation of the plant is carried out by producing an expression cassette comprising a lipase gene and a promoter controlling the expression of a specific protein of the seed, and introducing this expression cassette into the genome of the plant so as to express the lipase in the compartments of the seed where the specified protein accumulates, the lipids and the lipase are brought into contact by simple crushing.

In the case of rapeseed, the promoter of the protein used is advantageously the napine promoter, which permits a large accumulation of lipase in the protein bodies of the seed, separated from the lipid globules.

The procedure 1B outlined above may be used regardless of the type of oleaginous plant, for example by choosing the constituent promoter 35S of CaMV (cauliflower mosaic virus) and the tobacco address sequence PR-S so as to direct the secretion of the produced lipases to the extracellular compartments. In this case too the lipids and lipases are brought into contact by simple crushing.

The procedure (2) outlined above may be used regardless of the type of oleaginous plant, for example by choosing the protease inhibition promoter isolated from potatoes, which controls gene expression in the case of injury or damage. The induction treatment that initiates the synthesis of the lipases may in this case be shelling or hulling of the seeds, carried out before crushing.

Regardless of the procedure that is chosen, preferably a gene is used coding for a non-specific lipase, i.e. characterized by a non-specific hydrolytic activity, in order to achieve a complete hydrolysis of the lipids accumulated by the plant and prevent interfering saponification reactions. However, for certain uses of fatty acids it is possible to cause the plant to produce lipases of specific hydrolytic activity so as to promote a certain type of hydrolysis (for example: monoacylglycerol lipase from penicyllium camembertii, effecting the hydrolysis of only one of the three fatty acid-glycerol bonds, so as to produce diacylglycerols).

In particular there may be used non-specific lipase genes, characterized by the following sequences or by sequences similar to the following sequences (the arrows define the coding part):

```
                    SEQUENCE I (SEQ ID NO: 1)
          ▼
        ▼
    1 GATGACAACT TGGTTGGTGG CATGACTTTG GACTTACCCA GCGATGCTCC

51 TCCTATCAGC CTCTCTAGCT CTACCAACAG CGCCTCTGAT GGTGGTAAGG

101 TTGTTGCTGC TACTACTGCT CAGATCCAAG AGTTCACCAA GTATGCTGGT

151 ATCGCTGCCA CTGCCTACTG TCGTTCTGTT GTCCCTGGTA ACAAGTGGGA

201 TTGTGTCCAA TGTCAAAAGT GGGTTCCTGA TGGCAAGATC ATCACTACCT

251 TTACCTCCTT GCTTTCCGAT ACAAATGGTT ACGTCTTGAG AAGTGATAAA

301 CAAAAGACCA TTTATCTTGT TTTCCGTGGT ACCAACTCCT TCAGAAGTGC

351 CATCACTGAT ATCGTCTTCA ACTTTTCTGA CTACAAGCCT GTCAAGGGCG

401 CCAAAGTTCA TGCTGGTTTC CTTTCCTCTT ATGAGCAAGT TGTCAATGAC

451 TATTTCCCTG TCGTCCAAGA ACAATTGACC GCCCACCCTA CTTATAAGGT

501 CATCGTTACC GGTCACTCAC TCGGTGGTGC ACAAGCTTTG CTTGCCGGTA

551 TGGATCTCTA CCAACGTGAA CCAAGATTGT CTCCCAAGAA TTTGAGCATC

601 TTCACTGTCG GTGGTCCTCG TGTTGGTAAC CCCACCTTTG CTTACTATGT

651 TGAATCCACC GGTATCCCTT TCCAACGTAC CGTTCACAAG AGAGATATCG

701 TTCCTCACGT TCCTCCTCAA TCCTTCGGAT TCCTTCATCC CGGTGTTGAA
```

-continued

751 TCTTGGATGA AGTCTGGTAC TTCCAACGTT CAAATCTGTA CTTCTGAAAT

801 TGAAACCAAG GATTGCAGTA ACTCTATCGT TCCTTTCACC TCTATCCTTG

851 ACCACTTGAG TTACTTTGAT ATCAACGAAG GAAGCTGTTT GTAAAACACT

901 TGACGTGTTA CTCTAATTTT ATAATAAAAT TAAGTTTTTA TACAAT

SEQUENCE II (SEQ ID NO: 2)

1 GTCGACCATT TCAGCCTGTT TTGCTCGCAA AACGACGCCG CGGGCGTGCG

51 CTACCGCACA CTCCGTCGCT GGGCGTTGTG CGGGGAAGAT TCAAACGAGC

101 GTTTCGCGCC GTAACAACCC GCTCTCTTCC GCTCTGCCAC GCAGGTTATG

151 ACCGGCCGCC AGGAAGCCGC GGATTTCCTG GCCTGGAGGA AAAAAGCCGA

201 AGCTGGCACG GTTCCTGGCG CAAGGGACAG CGAAGCGGTT CTCCCGGAAG

251 GATTCGGGCG ATGGCTGGCA GGACGCGCCC CTCGGCCCCA TCAACCTGAG
                      ▼
301 ATGAGAACAA CATGAAGAAG AAGTCTCTGC TCCCCCTCGG CCTGGCCATC

351 GGTCTCGCCT CTCTCGCTGC CAGCCCTCTG ATCCAGGCCA GCACCTACAC

401 CCAGACCAAA TACCCCATCG TGCTGGCCCA CGGCATGCTC GGCTTCGACA

451 ACATCCTCGG GGTCGACTAC TGGTTCGGCA TTCCCAGCGC CTTGCGCCGT

501 GACGGTGCCC AGGTCTACGT CACCGAAGTC AGCCAGTTGG ACACCTCGGA

551 AGTCCGCGGC GAGCAGTTGC TGCAACAGGT GGAGGAAATC GTCGCCCTCA

601 GCGGCCAGCC CAAGGTCAAC CTGATCGGCC ACAGCCACGG CGGGCCGACC

651 ATCCGCTACG TCGCCGCCGT ACGTCCCGAC CTGATCGCTT CCGCCACCAG

701 CGTCGGCGCC CCGCACAAGG GTTCGGACAC CGCCGACTTC CTGCGCCAGA

751 TCCCACCGGG TTCGGCCGGC GAGGCAGTCC TCTCCGGGCT GGTCAACAGC

801 CTCGGCGCGC TGATCAGCTT CCTTTCCAGC GGCAGCACCG GTACGCAGAA

851 TTCACTGGGC TCGCTGGAGT CGCTGAACAG CGAGGGTGCC GCGCGCTTCA

901 ACGCCAAGTA CCCGCAGGGC ATCCCCACCT CGGCCTGCGG CGAAGGCGCC

951 TACAAGGTCA ACGGCGTGAG CTATTACTCC TGGAGCGGTT CCTCGCCGCT

1001 GACCAACTTC CTCGATCCGA GCGACGCCTT CCTCGGCGCC TCGTCGCTGA

1051 CCTTCAAGAA CGGCACCGCC AACGACGGCC TGGTCGGCAC CTGCAGTTCG

1101 CACCTGGGCA TGGTGATCCG CGACAACTAC CGGATGAACC ACCTGGACGA

1151 GGTGAACCAG GTCTTCGGCC TCACCAGCCT GTTCGAGACC AGCCCGGTCA
                                                           ▼
1201 GCGTCTACCG CCAGCACGCC AACCGCCTGA GAACGCCAG CCTGTAG

SEQUENCE III (SEQ ID NO: 3)

1 GGGTGCATGC CAGCTCCCAC CGGACACCTG GCCCGTCGCT GAAACGTGTT
                                                 ▼
 51 TTCGCTTTCT CTACAAATCC AACAACAGAG AGGCACTACC ATGGGTATCT

101 TTGACTATAA AAACCTTGGC ACCGAGGGTT CCAAAACGTT CTTCGCCGAT

151 GCCATGGCGA TCACGTTGTA TTCCTATCAC AACCTGGATA ACGGCTTTGC

201 CGTGGGCTAC CAGCACAACG GGTTGGGCTT GGGGCTACCG GCCACGCTGG

251 TCGGTGCGCT GCTCGGCAGC ACGGATTCCC AGGGCGTGAT CCCTGGCATC

301 CCGTGGAACC CGGATTCAGA AAAAGCCGCC CTTGAGGCGG TGCAGAAAGC

```
351 CGGTTGGACA CCGATCAGCG CCAGTGCCCT GGGCTACGCC GGCAAGGTCG
401 ATGCACGTGG CACCTTCTTT GGGGAAAAAG CCGGCTACAC CACGGCCCAG
451 GTCGAGGTAC TCGGCAAATA CGATGACGCC GGCAAGCTGC TCGAAATCGG
501 CATCGGTTTT CGTGGCACTT CGGGGCCACG GGAAACCTTG ATCAGCGACT
551 CGATCGGCGA CTTGATCAGC GATCTGCTCG CGGCCCTGGG GCCCAAGGAT
601 TACGCGAAAA ACTACGCCGG CGAAGCCTTC GGCGGCTTGC TCAAGAATGT
651 TGCCGACTAC GCCGGTGCCC ATGGCCTGAC CGGCAAGGAC GTGGTGGTCA
701 GCGGCCACAG CCTGGGCGGG CTGGCGGTCA ACAGCATGGC GGACTTGAGC
751 AACTACAAAT GGGCGGGGTT CTACAAGGAC GCCAACTATG TTGCCTATGC
801 CTCGCCGACC CAGAGTGCCG GCGACAAGGT GCTCAATATC GGTTACGAAA
851 ACGACCCGGT GTTCCGCGCG CTGGACGGCT CGTCGTTTAA CCTGTCGTCG
901 CTGGGCGTGC ACGACAAACC CCACGAGTCC ACCACCGATA ACATCGTCAG
951 CTTCAACGAC CACTACGCCT CGACGCTGTG GAATGTGCTG CCGTTTTCCA
1001 TCGTCAACCT GCCCACCTGG GTCTCGCATT TGCCGACGGC GTACGGCGAT
1051 GGCATGACGC GCATCCTCGA GTCCGGCTTC TACGACCAGA TGACCCGTGA
1101 CTCCACGGTG ATTGTTGCCA ACCTGTCCGA TCCGGCGCGG GCCAACACCT
1151 GGGTGCAGGA CCTCAACCGC AATGCCGAGC CCCACAAGGG CAACACGTTC
1201 ATCATCGGCA GCGACGGCAA CGACCTGATC CAGGGCGGCA ACGGTGCGGA
1251 CTTTATCGAG GGTGGCAAAG GCAACGACAC GATCCGCGAC AACAGCGGGC
1301 ACAACACCTT TTTGTTCAGC GGCCACTTTG GCAATGATCG CGTGATTGGC
1351 TACCAGCCCA CCGACAAACT GGTGTTCAAG GACGTGCAAG GAAGCACCGA
1401 CCTGCGTGAC CACGCGAAGG TGGTCGGCGC CGATACGGTG CTTACGTTTG
1451 GGGCCGACTC GGTGACGCTG GTCGGCGTGG GGCATGGCGG GCTGTGGACG
                                ▼
1501 GAGGGCGTGG TGATCGGCTG ATTACTCACG CAACCGATCA GTGCCAGTGC
1551 TGCCCCCGCC AGCCACCGCC CCAATTGGGC CGGTGGGGGT AGCCATAGCC
            SEQUENCE IV (SEQ ID NO: 4)
   1 GGGCGATGGC TGGCAGGACG CGCCCCTCGG CCCCATCAAC CTGAGATGAG
  51 AACAACATGA AGAAGAAGTC TCTGCTCCCC CTCGGCCTGG CCATCGGCCT
                                ▼
 101 CGCCTCTCTC GCTGCCAGCC CTCTGATCCA GGCCAGCACC TACACCCAGA
 151 CCAAATACCC CATCGTGCTG GCCCACGGCA TGCTCGGCTT CGACAATATC
 201 CTCGGGGTCG ACTACTGGTT CGGCATTCCC AGCGCCTTGC GCCGTGACGG
 251 TGCCCAGGTC TACGTCACCG AAGTCAGCCA GTTGGACACC TCGGAAGTCC
 301 GCGGCGAGCA GTTGCTGCAA CAGGTGGAGG AAATCGTCGC CCTCAGCGGC
 351 CAGCCCAAGG TCAACCTGAT CGGCCACAGC CACGGCGGGC CGACCATCCG
 401 CTACGTCGCC GCCGTACGTC CCGACCTGAT GCCTTCCGCC ACCAGCGTCG
 451 GCGCCCCGCA CAAGGGTTCG ACACCGCCG ACTTCCTGCG CCAGATCCCA
 501 CCGGGTTCGG CCGGCGAGGC AGTCCTCTCC GGGCTGGTCA ACAGCCTCGG
 551 CGCGCTGATC AGCTTCCTTT CCAGCGGCAG CGCCGGTACG CAGAATTCAC
 601 TGGGCTCGCT GGAGTCGCTG AACAGCGAGG GGGCCGCGCG CTTCAACGCC
 651 AAGTACCCGC AGGGCATCCC CACCTCGGCC TGCGGCGAAG GCGCCTACAA
```

```
 701 GGTCAACGGC GTGAGCTATT ACTCCTGGAG CGGTTCCTCG CCGCTGACCA
 751 ACTTCCTCGA TCCGAGCGAC GCCTTCCTCG GCGCCTCGTC GCTGACCTTC
 801 AAGAACGGCA CCGCCAACGA CGGCCTGGTC GGCACCTGCA GTTCGCACCT
 851 GGGCATGGTG ATCCGCGACA ACTACCGGAT GAACCACCTG GACGAGGTGA
 901 ACCAGGTCTT CGGCCTCACC AGCCTGTTCG AGACCAGCCC GGTCAGCGTC
                                              ▼
 951 TACCGCCAGC ACGCCAACCG CCTGAAGAAC GCCAGCCTGT AGGACCCCGG
1001 CCGGGGCCTC GGCCCCGGCC CTTTCCCGGA AGCCCCCTCG CGTGAAGAAA
1051 ATCCTCCTGC TGATTCCACT GGCGTTCGCC GCCAGCCTGG CCTGGTTCGT
```

<u>SEQUENCE V (SEQ ID NO: 5)</u>

▼
```
   1 CAGGCCCCCA CGGCCGTTCT TAATGGCAAC GAGGTCATCT CTGGTGTCCT
  51 TGGGGCAAG GTTGATACCT TAAGGGAAT TCCATTTGCT GACCCTCCTG
 101 TTGGTGACTT GCGGTTCAAG CACCCCCAGC CTTTCACTGG ATCCTACCAG
 151 GGTCTTAAGG CCAACGACTT CAGCTCTGCT TGTATGCAGC TTGATCCTGG
 201 CAATGCCATT TCTTGGCTTG ACAAAGTCGT GGGCTTGGGA AAGATTCTTC
 251 CTGATAACCT TAGAGGCCCT CTTTATGACA TGGCCCAGGG TAGTGTCTCC
 301 ATGAATGAGG ACTGTCTCTA CCTTAACGTT TTCCGCCCTG CTGGCACCAA
 351 GCCTGATGCT AAGCTCCCCG TCATGGTTTG GATTTACGGT GGTGCCTTTG
 401 TGTTTGGTTC TTCTGCTTCT TACCCTGGTA ACGGCTACGT CAAGGAGAGT
 451 GTGGAAATGG CCAGCCTGT TGTGTTTGTT TCCATCAACT ACCGTACCGG
 501 CCCCTATGGA TTCCTGGGTG GTGATGCCAT CACCGCTGAG GGTAACACCA
 551 ACGCTGGTCT GCACGACCAG CGCAAGGGTC TCGAGTGGGT TAGCGACAAC
 601 ATTGCCAACT TGGTGGTGA TCCCGACAAG GTCATGATTT TCGGTGAGTC
 651 CGCTGGTGCC ATGAGTGTTG CTCACCAGCT TGTTGCCTAC GGTGGTGACA
 701 ACACCTACAA CGGAAAGAAG CTTTTCCACT CTGCCATTCT TCAGTCTGGC
 751 GGTCCTCTTC CTTACTTTGA CTCTACTTCT GTTGGTCCCG AGAGTGCCTA
 801 CAGCAGATTT GCTCAGTATG CCGGATGTGA TGCCAGCGCC AGTGACAATG
 851 AAACTCTGGC TTGTCTCCGC AGCAAGTCCA GCGATGTCTT GCACAGTGCC
 901 CAGAACTCGT ACGATCTCAA GGACCTGTTT GGCCTGCTCC CTCAATTCCT
 951 TGGATTTGGT CCCAGACCCG ACGGCAACAT TATTCCCGAT GCCGCTTATG
1001 AGCTCTACCG CAGCGGTAGA TACGCCAAGG TTCCCTACAT TACTGGTAAC
1051 CAGGAGGATG AGGGTACTAT TCTTGCCCCC GTTGCTATTA ATGCTACCAC
1101 GACTCCCCAT GTTAAGAAGT GGTTGAAGTA CATTTGTAGC GAGGCTTCTG
1151 ACGCTTCGCT TGATCGTGTT TTGTCGCTCT ACCCCGGCTC TTGGTCGGAG
1201 GGTGCGCCAT TCCGCACTGG TATTCTTAAT GCTCTGACCC CTCAGTTCAA
1251 GCGCATTGCT GCCATTTTCA CTGATTTGCT GTTCCAGTCT CCTCGTCGTG
1301 TTATGCTTAA CGCTACCAAG GACGTCAACC GCTGGACTTA CCTTGCCACC
1351 CAGCTCCATA ACCTCGTTCC ATTTTTGGGT ACTTTCCATG GTAGTGATCT
1401 TCTTTTCCAA TACTACGTGG ACCTTGGCCC ATCTTCTGCT TACCGCCGCT
1451 ACTTTATCTC GTTTGCCAAC CACCACGACC CCAACGTTGG CACCAACCTG
```

```
                                                            -continued
1501 AAACAGTGGG ATATGTACAC TGATGCAGGC AAGGAGATGC TTCAGATTCA 1551 TATGGTTGGT AACTCTATGA GAACTGACGA CTTTAGAATC GAGGGAATCT
                                                  ▼
1601 CGAACTTTGA GTCTGACGTT ACTCTCTTCG GTTAA

SEQUENCE VI (SEQ ID NO: 6)

1                                                        ▼
   1 ATGGAGCTCG CTCTTGCGCT CCTGCTCATT GCCTCGGTGG CTGCTGCCCC

51 CACCGCCACG CTCGCCAACG GCGACACCAT CACCGGTCTC AACGCCATCA

101 TCAACGAGGC GTTCCTCGGC ATTCCCTTTG CCGAGCCGCC GGTGGGCAAC

151 CTCCGCTTCA AGGACCCCGT GCCGTACTCC GGCTCGCTCG ATGGCCAGAA

201 GTTCACGCTG TACGGCCCGC TGTGCATGCA GCAGAACCCC GAGGGCACCT

251 ACGAGGAGAA CCTCCCCAAG GCAGCGCTCG ACTTGGTGAT GCAGTCCAAG

301 GTGTTTGAGG CGGTGCTGCC GCTGAGCGAG GACTGTCTCA CCATCAACGT

351 GGTGCGGCCG CCGGGCACCA AGGCGGGTGC CAACCTCCCG GTGATGCTCT

401 GGATCTTTGG CGGCGGGTTT GAGGTGGGTG GCACCAGCAC CTTCCCTCCC

451 GCCCAGATGA TCACCAAGAG CATTGCCATG GGCAAGCCCA TCATCCACGT

501 GAGCGTCAAC TACCGCGTGT CGTCGTGGGG GTTCTTGGCT GGCGACGAGA

551 TCAAGGCCGA GGGCAGTGCC AACGCCGGTT TGAAGGACCA GCGCTTGGGC

601 ATGCAGTGGG TGGCGGACAA CATTGCGGCG TTTGGCGGCG ACCCGACCAA

651 GGTGACCATC TTTGGCGAGC TGGCGGGCAG CATGTCGGTC ATGTGCCACA

701 TTCTCTGGAA CGACGGCGAC AACACGTACA AGGGCAAGCC GCTCTTCCGC

751 GCGGGCATCA TGCAGCTGGG GGCCATGGTG CCGCTGGACG CCGTGGACGG

801 CATCTACGGC AACGAGATCT TTGACCTCTT GGCGTCGAAC GCGGGCTGCG

851 GCAGCGCCAG CGACAAGCTT GCGTGCTTGC GCGGTGTGCT GAGCGACACG

901 TTGGAGGACG CCACCAACAA CACCCCTGGG TTCTTGGCGT ACTCCTCGTT

951 GCGGTTGCTG TACCTCCCCC GGCCCGACGG CGTGAACATC ACCGACGACA

1001 TGTACGCCTT GGTGCGCGAG GGCAAGTATG CCAACATCCC TGTGATCATC

1051 GGCGACCAGA ACGACGAGGG CACCTTCTTT GGCACCCTGC TGTTGAACGT

1101 GACCACGGAT GCCCAGGCCC GCGAGTACTT CAAGCAGCTG TTTGTCCACG

1151 CCAGCGACGC GGAGATCGAC ACGTTGATGA CGGCGTACCC CGGCGACATC

1201 ACCCAGGGCC TGCCGTTCGA CACGGGTATT CTCAACGCCC TCACCCCGCA

1251 GTTCAAGAGA ATCCTGGCGG TGCTCGGCGA CCTTGGCTTT ACGCTTGCTC

1301 GTCGCTACTT CCTCAACCAC TACACCGGCG GCACCAAGTA CTCATTCCTC

1351 CTGAAGCAGC TCCTGGGCTT GCCGGTGCTC GGAACGTTCC ACTCCAACGA

1401 CATTGTCTTC CAGGACTACT TGTTGGGCAG CGGCTCGCTC ATCTACAACA

1451 ACGCGTTCAT TGCGTTTGCC ACGGACTTGG ACCCCAACAC CGCGGGGTTG

1501 TTGGTGAAGT GGCCCGAGTA CACCAGCAGC CTGCAGCTGG GCAACAACTT

1551 GATGATGATC AACGCCTTGG GCTTGTACAC CGGCAAGGAC AACTTCCGCA
                                                          ▼
1601 CCGCCGGCTA CGACGCGTTG TTCTCCAACC CGCCGCTGTT CTTTGTGTAA
```

The identification of the six aforementioned sequences is as follows in the "EMBL" and "GENE BANK" databank:

SEQUENCE I (SEQ ID NO:1)

LOCUS:RCHLIPASE, 946 bp ss mRNA PLN 23/01/93
DEFINITION:*Rhizopus niveus* mRNA for lipase, partial sequence ACCESSION:D 12 680
SEQUENCE II (SEQ ID NO:2)
LOCUS:PALIPAG 1247 bp DNA BCT 21/07/93
DEFINITION:*P airuginosa* lip A gene for lipase
ACCESSION:X 63 390 S 43 732
SEQUENCE III (SEQ ID NO:3)
LOCUS:PSELIPASEE, 1700 bp ds-DNA BCT 15/04/92
DEFINITION:*Pseudomonas fluorescens* lipase gene, coplete cds
ACCESSION:M.86 350
SEQUENCE IV (SEQ ID NO:4)
LOCUS:PSELIPL, 1282 bp ds-DNA BCT 17/04/92
DEFINNITION:Pseudomonas sp. Lipl gene for lipase
ACCESSION:D 10166 D 90398
SEQUENCE V (SEQ ID NO:5)
LOCUS:GCU 02387, 1635 bp DNA PLN 07/10/93
DEFINITION:*Geotrichum candidum* NRRLY-553 Lipase gene, partial eds
ACCESSION:UO 2367
SEQUENCE VI (SEQ ID NO:6)
LOCUS:CCLIP1, 1733 bp DNA PLN 27/04/93
DEFINITION:C. Cylindracea LIP1 gene for lipase
ACCESSION:X 64703

The sequence I (SEQ ID NO:1) corresponds to a cDNA of *Rhizopus niveus,* the sequence II (SEQ ID NO:2) may be isolated from the genome of *Pseudomonas aeruginosa,* sequence III (SEQ ID NO:3) from *Pseudomonas fluorescens,* sequence IV (SEQ ID NO:4) from Pseudomonas sp, sequence V (SEQ ID NO:5) from *Geotricum candidum,* and sequence VI (SEQ ID NO:6) from *Candida cylindracea.*

In addition, the introduction of the expression cassette: lipase gene/expression promoter of this gene, into the genome of the oleaginous plant may be effected by any known protocol.

For example, according to the most common protocol at the present time, this expression cassette may be introduced into the genome of somatic cells of the plant by a transfer by means of the bacterium *Agrobacterium tumefaciens.* This introduction into the somatic cells of the plant may also be effected by any other known technique, in particular by electroporation, biolistics or by microinjection.

It is also possible to introduce the expression cassette into the genome of microspores of the plant by electroporation or biolistics.

In the protocol provided later by way of example, the technique of electroporation is described for introducing the cassettte into the microspores of rapeseed.

Reference may be made to the following document "P. J. J. Hooykaas and R. A. Schilperoort, TIBS August 1985, p. 305–309" for more details on the transfer technique by means of the bacterium *Agrobacterium tumefaciens.* It will be recalled that this technique consists in introducing the relevant expression cassette into the Ti plasmid of the bacterium, in particular by thermal shock, followed by contact between the bacterium and the leaf discs of the plant, allowing the whole to incubate until the expression cassette is transferred into the genome of the cells of the foliar discs, and cultivating these foliar discs on a succession of media to regenerate the transgenic plants.

Reference may also be made to the following document "J. A. Russell et al., In Vitro Cell. Dev. Biol., 1992, 28P, p. 97–105" for more details of the biolistics technique. It will be recalled that this technique consists in attaching the plasmid containing the expression cassette to gold or tungsten microspheres, shooting these microspheres by means of a particle gun onto the cells of the plant to be transformed, and cultivating these cells until regeneration of the transgenic plants has occurred.

Reference may be made to the following document "Crossway A and A1, 1986, Mol. Gen. Genet 202, 179–185" for more details of the technique of microinjection. It will be recalled that this technique consists in injecting the plasmid containing the expression cassette into protoplasts or very young embryos by means of microsyringes, and cultivating the protoplasts until regeneration of the transgenic plants has occurred.

After the lipase and lipids have been brought into contact by crushing, the mixture is left to incubate so as to effect enzymatic hydrolysis. This incubation is carried out under normal conditions, in particular between 20° C. and 60° C., for the time required to achieve a total or almost total hydrolysis.

The fatty acids produced by the hydrolysis are extracted and then worked up by any known process, in particular by liquid/liquid extraction using a non-polar solvent such as chloroform or hexane.

According to another procedure, it is possible to carry out an in situ conversion of the fatty acids to obtain fatty acid derivatives, which are then extracted. For example the fatty acids produced by the hydrolysis may be methylated in situ by mixing them with methanol under acid catalysis and ultrasound so as to convert the acids into methyl esters, which are then extracted by a liquid/liquid extraction using a non-polar solvent.

The present application provides, as a novel product, any oleaginous plant or oleaginous plant seed of a variety that is not protectable by a plant breeding certificate, which includes in its genome an expression cassette containing at least one gene coding for a lipase enzyme, associated with a promoter permitting an expression of the gene in cellular, extracellular or tissue compartments different from the lipid compartments of the plant or seed.

The promoter associated with the lipase gene may be a specific cellular expression or tissue expression promoter. This promoter may also be a constituent promoter, in which case the lipase gene is provided with an address sequence for cellular or extracellular compartments different from the lipid accumulation compartments.

The present application also covers any oleaginous plant or oleaginous plant seed of a variety that is not protectable by a plant breeding certificate, which includes in its genome an expression cassette having at least one gene coding for a lipase enzyme, associated with a promoter permitting an expression of the said gene by exogenous induction, in particular by a stress.

BRIEF DESCRIPTION OF THE DRAWINGS

The following description together with the accompanying diagram provides by way of example a protocol for implementing the process of the invention.

DETAILED DESCRIPTION OF THE INVENTION

1. PROTOCOL FOR OBTAINING TRANSGENIC RAPESEED PLANTS EXPRESSING A LIPASE GENE a) Plant material Rapeseed (*Brassica napus*, Var Tapidor) seeds are used, which are commercially available.

The seeds are sown in a greenhouse and cultivated under normal conditions. The state of health of the plants is strictly monitored.

The young buds (size less than 3.5 mm) are picked, sterilized in sodium hypochlorite for 30 minutes, and the microspores are extracted from the anthers by crushing in a Waring Blender in the medium of Huang et al (Huang et al. 1990, Plant. Cell. Rep. 8, 594–597). After filtering through a 5 μm mesh size metal sieve, the microspores are recovered by centrifugation for 5 minutes at 100 xg (protocol described in Jardinaud et al., 1993, Plant. Sci. 93, 177–184).

b) Genetic structure

Figure 1:
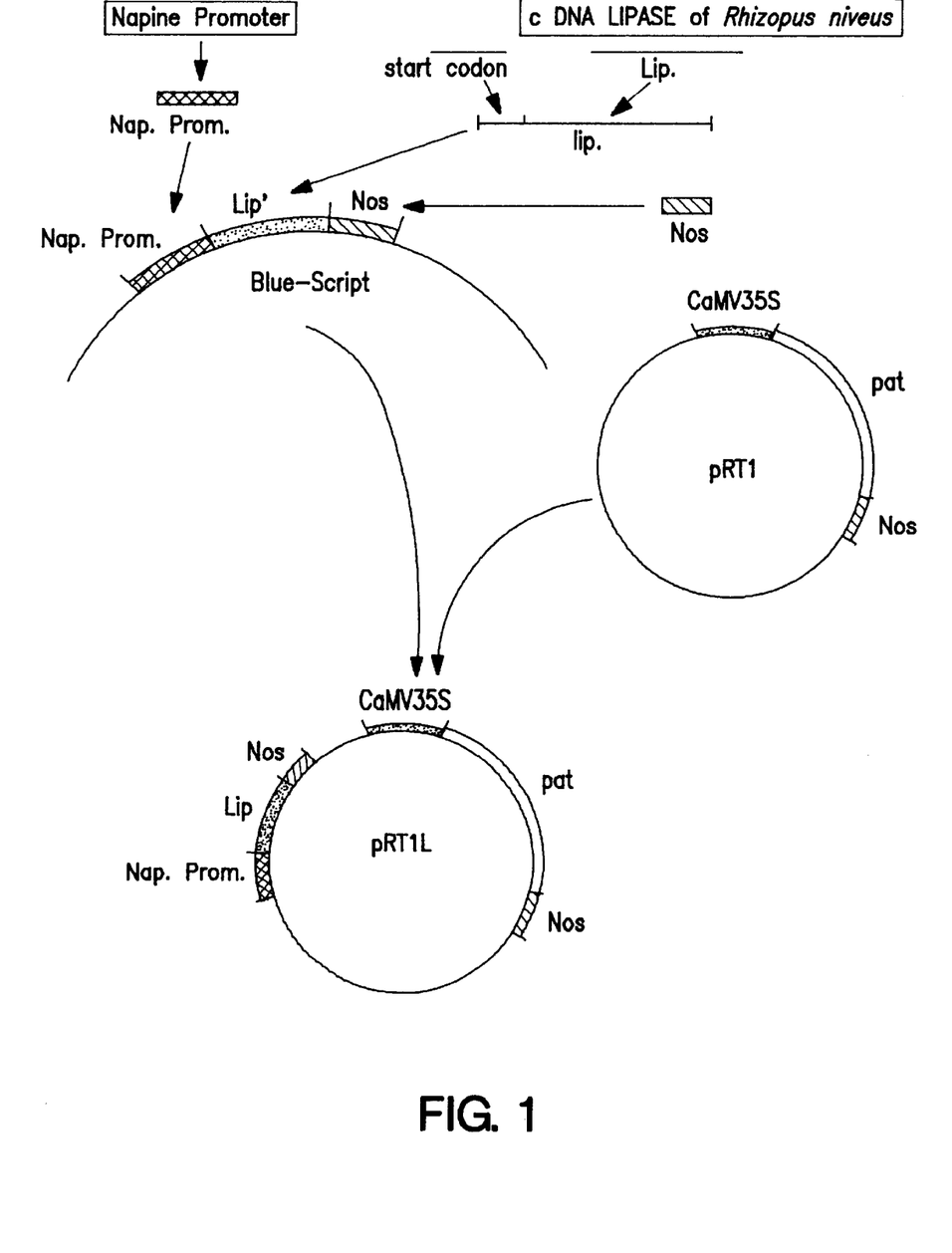
FIG. 1 of the diagram illustrates the preparation of the genetic material to be transferred.

The genetic structure that is adopted utilizes the napine promoter, the cDNA of *Rhizopus niveus* lipase and the NOS terminator. The napine promoter governs the expression of this protein in a protein compartment of the seed different from that in which the lipids accumulate. The whole arrangement is introduced into the PRT1 plasmid containing the pat selection gene used to screen the transformants so as to form the pRTlL structure.

Details of the structure are shown in FIG. 1 of the drawing.

The napine promoter designated "Prom. Nap" was isolated by Professor Rask's team (Stalberg K. et al, 1993, Plant Molecular Biology, 23:671–683). The *Rhizopus niveus* lipase cDNA, designated "Lip", was isolated by the Central Research Institute (Kugimiya et al., 1992, Biosci. Biotech. Biochem. 56, 716–719). An initiation codon, designated "start codon", compatible with the 5' end of the cDNA (available on the market) is grafted onto this end. A terminator designated NOS extracted from the pRT1 plasmid mentioned hereinbelow is grafted onto the 3' end, designated "lip", of the resultant arrangement, and the Nap promoter is grafted onto the 5' end.

The expression cassette thus obtained is introduced into a plasmid designated "Blue-Script" (commercial name) so that it can be amplified.

The amplified expression cassette is then extracted from "Blue-Script" and introduced into a plasmid designated pRT1, which was prepared by grafting the promoter designated CaMV35S onto the 5' end of the "pat" gene coding for phosphinothricine acetyl transferase (selection gene), and the NOS terminator onto the 3' end.

A plasmid designated pRTlL is obtained containing the desired expression cassette.

c) Gene transfer and production of transgenic plants

The microspores isolated in a) ($10^6$ microspores $ml^{-1}$) are suspended in Brewbaker and Kwack's medium (J. L. Brewbaker and B. H. Kwack, 1963, Am. J. Bot. 50, p. 859–865) containing 13% sucrose and adjusted to pH 5.9. 50 μg per ml of the pRTlL plasmid are added to the medium and electrical pulses of 400 V/cm are applied for 10 ms to the suspension by means of a "Jouan" electroporation apparatus (trademark) (TRX, GHT) delivering square wave pulses. After 20 minutes' rest the culture medium (Huang et al.) containing 100 mg/l of phosphinothricine is added to the microspores. The microspores are cultivated in the dark for 24 hrs at 35° C. and then at 25° C. After two weeks of cultivation an equal volume of new medium is added and the microspores are exposed to cycles of 16 hours of light per day followed by 8 hours of darkness.

After about 1 month the embryos are transferred to $B_5$ medium (Gamborg et al., 1979, Exp. Cell. Res. 50, 151–158) containing 1 ml/g of $G3A_3$ and 20 g/l of sucrose, to which 8 g/l of "Bacto Agar" (trademark) gelling agent is added.

The phosphinothricine-resistant regenerated plants are analyzed by Southern blotting so as to verify the presence in their genome of the sequence coding for lipase. The chromosome complement of the plants is doubled by colchicine (0.1 g/l plus a few drops of Teepol) and the resultant fertile diploid plant are self-fertilized.

The activity of the lipase is investigated in a limited number of seeds. The plants having seeds with the greatest lipase activity are retained and the seeds are used to propagate the plants until enough seeds are obtained to perform the hydrolysis experiments on the seed lipids with endogenous lipase.

2. ENZYMATIC HYDROLYSIS OF THE LIPIDS OF THE RESULTANT RAPESEED SEEDS

The seeds are crushed and the crushed material is placed in an incubator kept at a constant temperature of 40°. The crushed material is constantly agitated to increase the contact between the lipids and the lipase.

After 48 hours hydrolysis, the fatty acids are extracted with chloroform. The chloroform is evaporated and the fatty acids are recovered.

We claim:

1. A process for producing fatty acids or derivatives of fatty acids from oleaginous plants, which comprises:
   producing transgenic oleaginous plants having at least one lipase gene coding for a lipase enzyme, and associated with said lipase gene, a promoter permitting an expression of said lipase gene either in cellular, extracellular or tissue compartments different from those in which the plant lipids accumulate, or by exogenous induction,
   collecting the seeds or fruits containing the lipids of said plants,
   crushing the seeds or fruits, if necessary after induction treatment, so as to bring into contact the lipids and the lipase contained in said seeds or fruits,
   allowing the whole mixture to incubate to effect an enzymatic hydrolysis of the lipids of the crushed material under the catalytic action of the lipase contained in the crushed material, and
   extracting or converting the fatty acids resulting from the hydrolysis to obtain the desired fatty acid derivatives.

2. Process according to claim 1, in which the transgenic oleaginous plants are produced by effecting a genetic transformation of a natural oleaginous plant, causing the genetically transformed plant to-reproduce sexually so as to produce transgenic seeds and using the said transgenic seeds in order to obtain transgenic plant progeny.

3. Process according to claim 2, wherein:
   the genetic transformation of the plant is effected by producing an expression cassette containing a lipase gene and a promoter controlling the expression of a specific protein in the seed, and introducing this expression cassette into the genome of the plant so as to express the lipase in the compartments of the seed where the specific protein accumulates,
   the lipids and the lipase are brought into contact by simple crushing.

4. Process according to claim 3, wherein said oleoginous plants are rapeseed plants, and the genetic transformation is effected starting from an expression cassette comprising a lipase gene and a napine promoter.

5. Process according to claim 2, wherein:
   the genetic transformation of the plant is effected by producing an expression cassette containing a lipase gene and a promoter that can be controlled in an exogenous manner, and introducing this expression cassette into the genome of the plant,
   an induction treatment is applied to the seeds and fruits before crushing so as to induce synthesis of the lipase.

6. Process according to claim 5, wherein:
   the genetic transformation is carried out from an expression cassette comprising a lipase gene and a stress promoter,
   the induction treatment consists of a physical stress applied to the seeds or fruits before crushing.

7. Process according to claim 2, wherein:
   the genetic transformation of the plant is effected by producing an expression cassette comprising a constitutive promoter and a lipase gene provided with a signal sequence for cellular or extracellular compartments different from those where the lipids accumulate,
   the lipids and lipase are brought into contact by simple crushing.

8. Process according to claim 2, in which the genetic transformation of the plant is carried out by producing an expression cassette containing the lipase gene and the associated promoter, and by introducing this expression cassette into the genome of somatic cells of the plant by a transfer selected from the group consisting of bacterium Agrobacterium tumefaciens, electroporation, biolistics, and microinjection.

9. Process according to claim 2, in which the genetic transformation of the plant is carried out by producing an expression cassette containing the lipase gene and the associated promoter, and by introducing this expression cassette into the genome of microspores of the plant by electroporation or biolistics.

10. Process according to claim 1, wherein transgenic plants are produced containing a lipase gene having a non-specific hydrolytic activity in order to achieve a complete hydrolysis of the lipids.

11. Process according to claim 8, wherein transgenic plants are produced containing a lipase gene having a sequence identical or similar to one of SEQ ID NOS:1–6.

12. Process according to claim 1, in which the incubation to induce enzymatic hydrolysis is carried out at a temperature between 20° C. and 60° C.

13. Process according to claim 1, in which the extraction of the fatty acids produced by the hydrolysis is carried out by a liquid/liquid extraction using a non-polar solvent.

14. Process according to claim 1, in which the fatty acids produced by the hydrolysis are methylated in situ by contact with methanol under acid catalysis and ultrasound in order to convert them into methyl esters, the latter being extracted by a liquid/liquid extraction using a non-polar solvent.

15. A plant or plant seed, containing in its genome an expression cassette having at least one gene coding for an enzyme, associated with a promoter permitting an expression of said gene in cellular, extracellular or tissue compartments, wherein:

the plant or the plant seed is of an oleaginous type capable of producing lipids in specific lipid compartments, the coding gene is a gene coding for a lipase enzyme capable of hydrolyzing the lipids, the promoter associated with the gene is of the type permitting an expression of the gene in compartments different from the lipid compartments of the plant or seed so as to prevent contact between lipids and lipases produced by the plant.

16. The plant or seed according to claim 15, in which the promoter associated with the lipase gene is a cellular expression promoter or specific tissue promoter.

17. The plant or seed according to claim 15, in which the lipase gene is provided with a signal sequence for cellular or extracellular compartments different from the lipid accumulation compartments, the promoter being a constitutive promoter.

18. A plant or plant seed, containing in its genome an expression cassette having at least one gene coding for an enzyme, associated with a promoter permitting an expression of said gene, wherein:

the plant or the plant seed is of an oleaginous type capable of producing lipids in specific lipid compartments, the coding gene is a gene coding for a lipase enzyme capable of hydrolyzing the lipids, the promoter associated with the gene is of the exogenous induction type, capable of controlling the production of lipase under the action of an exogenous signal.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 946 base pairs
      (B) TYPE: nucleic acid
      (C) STRANDEDNESS: single
      (D) TOPOLOGY: linear    (ii) MOLECULE TYPE: cDNA    (xi) SEQUENCE DESCRIPTION: SEQ ID NO:1:

```
GATGACAACT TGGTTGGTGG CATGACTTTG GACTTACCCA GCGATGCTCC TCCTATCAGC      60

CTCTCTAGCT CTACCAACAG CGCCTCTGAT GGTGGTAAGG TTGTTGCTGC TACTACTGCT     120
```

```
CAGATCCAAG AGTTCACCAA GTATGCTGGT ATCGCTGCCA CTGCCTACTG TCGTTCTGTT      180

GTCCCTGGTA ACAAGTGGGA TTGTGTCCAA TGTCAAAAGT GGGTTCCTGA TGGCAAGATC      240

ATCACTACCT TTACCTCCTT GCTTTCCGAT ACAAATGGTT ACGTCTTGAG AAGTGATAAA      300

CAAAAGACCA TTTATCTTGT TTTCCGTGGT ACCAACTCCT TCAGAAGTGC CATCACTGAT      360

ATCGTCTTCA ACTTTTCTGA CTACAAGCCT GTCAAGGGCG CCAAAGTTCA TGCTGGTTTC      420

CTTTCCTCTT ATGAGCAAGT TGTCAATGAC TATTTCCCTG TCGTCCAAGA ACAATTGACC      480

GCCCACCCTA CTTATAAGGT CATCGTTACC GGTCACTCAC TCGGTGGTGC ACAAGCTTTG      540

CTTGCCGGTA TGGATCTCTA CCAACGTGAA CCAAGATTGT CTCCCAAGAA TTTGAGCATC      600

TTCACTGTCG GTGGTCCTCG TGTTGGTAAC CCCACCTTTG CTTACTATGT TGAATCCACC      660

GGTATCCCTT TCCAACGTAC CGTTCACAAG AGAGATATCG TTCCTCACGT TCCTCCTCAA      720

TCCTTCGGAT TCCTTCATCC CGGTGTTGAA TCTTGGATGA AGTCTGGTAC TTCCAACGTT      780

CAAATCTGTA CTTCTGAAAT TGAAACCAAG GATTGCAGTA ACTCTATCGT TCCTTTCACC      840

TCTATCCTTG ACCACTTGAG TTACTTTGAT ATCAACGAAG GAAGCTGTTT GTAAAACACT      900

TGACGTGTTA CTCTAATTTT ATAATAAAAT TAAGTTTTTA TACAAT                    946

(2) INFORMATION FOR SEQ ID NO:2:

(i) SEQUENCE CHARACTERISTICS:
        (A) LENGTH: 1257 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GTCGACCATT TCAGCCTGTT TTGCTCGCAA AACGACGCCG CGGGCGTGCG CTACCGCACA       60

CTCCGTCGCT GGGCGTTGTG CGGGGAAGAT TCAAACGAGC GTTTCGCGCC GTAACAACCC      120

GCTCTCTTCC GCTCTGCCAC GCAGGTTATG ACCGGCCGCC AGGAAGCCGC GGATTTCCTG      180

GCCTGGAGGA AAAAAGCCGA AGCTGGCACG GTTCCTGGCG CAAGGGACAG CGAAGCGGTT      240

CTCCCGGAAG GATTCGGGCG ATGGCTGGCA GGACGCGCCC CTCGGCCCCA TCAACCTGAG      300

ATGAGAACAA CATGAAGAAG AAGTCTCTGC TCCCCCTCGG CCTGGCCATC GGTCTCGCCT      360

CTCTCGCTGC CAGCCCTCTG ATCCAGGCCA GCACCTACAC CCAGACCAAA TACCCCATCG      420

TGCTGGCCCA CGGCATGCTC GGCTTCGACA ACATCCTCGG GGTCGACTAC TGGTTCGGCA      480

TTCCCAGCGC CTTGCGCCGT GACGGTGCCC AGGTCTACGT CACCGAAGTC AGCCAGTTGG      540

ACACCTCGGA AGTCCGCGGC GAGCAGTTGC TGCAACAGGT GGAGGAAATC GTCGCCCTCA      600

GCGGCCAGCC CAAGGTCAAC CTGATCGGCC ACAGCCACGG CGGGCCGACC ATCCGCTACG      660

TCGCCGCCGT ACGTCCCGAC CTGATCGCTT CCGCCACCAG CGTCGGCGCC CCGCACAAGG      720

GTTCGGACAC CGCCGACTTC CTGCGCCAGA TCCCACCGGG TTCGGCCGGC GAGGCAGTCC      780

TCTCCGGGCT GGTCAACAGC CTCGGCGCGC TGATCAGCTT CCTTTCCAGC GGCAGCACCG      840

GTACGCAGAA TTCACTGGGC TCGCTGGAGT CGCTGAACAG CGAGGGTGCC GCGCGCTTCA      900

ACGCCAAGTA CCCGCAGGGC ATCCCCACCT CGGCCTGCGG CGAAGGCGCC TACAAGGTCA      960

ACGGCGTGAG CTATTACTCC TGGAGCGGTT CCTCGCCGCT GACCAACTTC CTCGATCCGA     1020

GCGACGCCTT CCTCGGCGCC CCTCGGCGCC TCGTCGCTGA CCTTCAAGAA CGGCACCGCC     1080

AACGACGGCC TGGTCGGCAC CTGCAGTTCG CACCTGGGCA TGGTGATCCG CGACAACTAC     1140

CGGATGAACC ACCTGGACGA GGTGAACCAG GTCTTCGGCC TCACCAGCCT GTTCGAGACC     1200
```

```
AGCCCGGTCA GCGTCTACCG CCAGCACGCC AACCGCCTGA AGAACGCCAG CCTGTAG      1257
```

(2) INFORMATION FOR SEQ ID NO:3:

(i) SEQUENCE CHARACTERISTICS:
        (A) LENGTH: 1600 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:3:

```
GGGTGCATGC CAGCTCCCAC CGGACACCTG GCCCGTCGCT GAAACGTGTT TTCGCTTTCT    60
CTACAAATCC AACAACAGAG AGGCACTACC ATGGGTATCT TTGACTATAA AAACCTTGGC   120
ACCGAGGGTT CCAAAACGTT GTTCGCCGAT GCCATGGCGA TCACGTTGTA TTCCTATCAC   180
AACCTGGATA ACGGCTTTGC CGTGGGCTAC CAGCACAACG GGTTGGGCTT GGGGCTACCG   240
GCCACGCTGG TCGGTGCGCT GCTCGGCAGC ACGGATTCCC AGGGCGTGAT CCCTGGCATC   300
CCGTGGAACC CGGATTCAGA AAAAGCCGCC CTTGAGGCGT GCAGAAAGC CGGTTGGACA    360
CCGATCAGCG CCAGTGCCCT GGGCTACGCC GGCAAGGTCG ATGCACGTGG CACCTTCTTT   420
GGGGAAAAAG CCGGCTACAC CACGGCCCAG GTCGAGGTAC TCGGCAAATA CGATGACGCC   480
GGCAAGCTGC TCGAAATCGG CATCGGTTTT CGTGGCACTT CGGGGCCACG GGAAACCTTG   540
ATCAGCGACT CGATCGGCGA CTTGATCAGC GATCTGCTCG CGGCCCTGGG GCCCAAGGAT   600
TACGCGAAAA ACTACGCCGG CGAAGCCTTC GGCGGCTTGC TCAAGAATGT TGCCGACTAC   660
GCCGGTGCCC ATGGCCTGAC CGGCAAGGAC GTGGTGGTCA GCGGCCACAG CCTGGGCGGG   720
CTGGCGGTCA ACAGCATGGC GGACTTGAGC AACTACAAAT GGGCGGGGTT CTACAAGGAC   780
GCCAACTATG TTGCCTATGC CTCGCCGACC CAGAGTGCCG GCGACAAGGT GCTCAATATC   840
GGTTACGAAA ACGACCCGGT GTTCCGCGCG CTGGACGGCT CGTCGTTTAA CCTGTCGTCG   900
CTGGGCGTGC ACGACAAACC CCACGAGTCC ACCACCGATA ACATCGTCAG CTTCAACGAC   960
CACTACGCCT CGACGCTGTG GAATGTGCTG CCGTTTTCCA TCGTCAACCT GCCCACCTGG  1020
GTCTCGCATT TGCCGACGGC GTACGGCGAT GGCATGACGC GCATCCTCGA GTCCGGCTTC  1080
TACGACCAGA TGACCCGTGA CTCCACGGTG ATTGTTGCCA ACCTGTCCGA TCCGGCGCGG  1140
GCCAACACCT GGGTGCAGGA CCTCAACCGC AATGCCGAGC CCCACAAGGG CAACACGTTC  1200
ATCATCGGCA GCGACGGCAA CGACCTGATC CAGGGCGGCA ACGGTGCGGA CTTTATCGAG  1260
GGTGGCAAAG GCAACGACAC GATCCGCGAC AACAGCGGGC ACAACACCTT TTTGTTCAGC  1320
GGCCACTTTG GCAATGATCG CGTGATTGGC TACCAGCCCA CCGACAAACT GGTGTTCAAG  1380
GACGTGCAAG GAAGCACCGA CCTGCGTGAC CACGCGAAGG TGGTCGGCGC CGATACGGTG  1440
CTTACGTTTG GGGCCGACTC GGTGACGCTG GTCGGCGTGG GGCATGGCGG GCTGTGGACG  1500
GAGGGCGTGG TGATCGGCTG ATTACTCACG CAACCGATCA GTGCCAGTGC TGCCCCCGCC  1560
AGCCACCGCC CCAATTGGGC CGGTGGGGGT AGCCATAGCC                        1600
```

(2) INFORMATION FOR SEQ ID NO:4:

(i) SEQUENCE CHARACTERISTICS:
        (A) LENGTH: 1100 base pairs
        (B) TYPE: nucleic acid
        (C) STRANDEDNESS: single
        (D) TOPOLOGY: linear     (ii) MOLECULE TYPE: cDNA (xi) SEQUENCE DESCRIPTION: SEQ ID NO:4:

```
GGGCGATGGC TGGCAGGACG CGCCCCTCGG CCCCATCAAC CTGAGATGAG AACAACATGA      60
AGAAGAAGTC TCTGCTCCCC CTCGGCCTGG CCATCGGCCT CGCCTCTCTC GCTGCCAGCC     120
CTCTGATCCA GGCCAGCACC TACACCCAGA CCAAATACCC CATCGTGCTG GCCCACGGCA     180
TGCTCGGCTT CGACAATATC CTCGGGGTCG ACTACTGGTT CGGCATTCCC AGCGCCTTGC     240
GCCGTGACGG TGCCCAGGTC TACGTCACCG AAGTCAGCCA GTTGGACACC TCGGAAGTCC     300
GCGGCGAGCA GTTGCTGCAA CAGGTGGAGG AAATCGTCGC CCTCAGCGGC CAGCCCAAGG     360
TCAACCTGAT CGGCCACAGC CACGGCGGGC CGACCATCCG CTACGTCGCC GCCGTACGTC     420
CCGACCTGAT GCCTTCCGCC ACCAGCGTCG GCGCCCCGCA CAAGGGTTCG GACACCGCCG     480
ACTTCCTGCG CCAGATCCCA CCGGGTTCGG CCGGCGAGGC AGTCCTCTCC GGGCTGGTCA     540
ACAGCCTCGG CGCGCTGATC AGCTTCCTTT CCAGCGGCAG CGCCGGTACG CAGAATTCAC     600
TGGGCTCGCT GGAGTCGCTG AACAGCGAGG GGGCCGCGCG CTTCAACGCC AAGTACCCGC     660
AGGGCATCCC CACCTCGGCC TGCGGCGAAG GCGCCTACAA GGTCAACGGC GTGAGCTATT     720
ACTCCTGGAG CGGTTCCTCG CCGCTGACCA ACTTCCTCGA TCCGAGCGAC GCCTTCCTCG     780
GCGCCTCGTC GCTGACCTTC AAGAACGGCA CCGCCAACGA CGGCCTGGTC GGCACCTGCA     840
GTTCGCACCT GGGCATGGTG ATCCGCGACA ACTACCGGAT GAACCACCTG GACGAGGTGA     900
ACCAGGTCTT CGGCCTCACC AGCCTGTTCG AGACCAGCCC GGTCAGCGTC TACCGCCAGC     960
ACGCCAACCG CCTGAAGAAC GCCAGCCTGT AGGACCCCGG CCGGGGCCTC GGCCCCGGCC    1020
CTTTCCCGGA AGCCCCCTCG CGTGAAGAAA ATCCTCCTGC TGATTCCACT GGCGTTCGCC    1080
GCCAGCCTGG CCTGGTTCGT                                                1100
```

(2) INFORMATION FOR SEQ ID NO:5:

(i) SEQUENCE CHARACTERISTICS:
        (A) LENGTH: 1635 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:5:

```
CAGGCCCCCA CGGCCGTTCT TAATGGCAAC GAGGTCATCT CTGGTGTCCT TGGGGGCAAG      60
GTTGATACCT TTAAGGGAAT TCCATTTGCT GACCCTCCTG TTGGTGACTT GCGGTTCAAG     120
CACCCCCAGC CTTTCACTGG ATCCTACCAG GGTCTTAAGG CCAACGACTT CAGCTCTGCT     180
TGTATGCAGC TTGATCCTGG CAATGCCATT TCTTGGCTTG ACAAAGTCGT GGGCTTGGGA     240
AAGATTCTTC CTGATAACCT TAGAGGCCCT CTTTATGACA TGGCCCAGGG TAGTGTCTCC     300
ATGAATGAGG ACTGTCTCTA CCTTAACGTT TTCCGCCCTG CTGGCACCAA GCCTGATGCT     360
AAGCTCCCCG TCATGGTTTG GATTTACGGT GGTGCCTTTG TGTTTGGTTC TTCTGCTTCT     420
TACCCTGGTA ACGGCTACGT CAAGGAGAGT GTGGAAATGG CCAGCCTGT TGTGTTTGTT     480
TCCATCAACT ACCGTACCGG CCCCTATGGA TTCCTGGGTG GTGATGCCAT CACCGCTGAG     540
GGTAACACCA ACGCTGGTCT GCACGACCAG CGCAAGGGTC TCGAGTGGGT TAGCGACAAC     600
ATTGCCAACT TGGTGGTGA TCCCGACAAG GTCATGATTT TCGGTGAGTC CGCTGGTGCC     660
ATGAGTGTTG CTCACCAGCT TGTTGCCTAC GGTGGTGACA ACACCTACAA CGGAAAGAAG     720
CTTTTCCACT CTGCCATTCT TCAGTCTGGC GGTCCTCTTC CTTACTTTGA CTCTACTTCT     780
```

```
GTTGGTCCCG AGAGTGCCTA CAGCAGATTT GCTCAGTATG CCGGATGTGA TGCCAGCGCC      840

AGTGACAATG AAACTCTGGC TTGTCTCCGC AGCAAGTCCA GCGATGTCTT GCACAGTGCC      900

CAGAACTCGT ACGATCTCAA GGACCTGTTT GGCCTGCTCC CTCAATTCCT TGGATTTGGT      960

CCCAGACCCG ACGGCAACAT TATTCCCGAT GCCGCTTATG AGCTCTACCG CAGCGGTAGA     1020

TACGCCAAGG TTCCCTACAT TACTGGTAAC CAGGAGGATG AGGGTACTAT TCTTGCCCCC     1080

GTTGCTATTA ATGCTACCAC GACTCCCCAT GTTAAGAAGT GGTTGAAGTA CATTTGTAGC     1140

GAGGCTTCTG ACGCTTCGCT TGATCGTGTT TTGTCGCTCT ACCCCGGCTC TTGGTCGGAG     1200

GGTGCGCCAT TCCGCACTGG TATTCTTAAT GCTCTGACCC CTCAGTTCAA GCGCATTGCT     1260

GCCATTTTCA CTGATTTGCT GTTCCAGTCT CCTCGTCGTG TTATGCTTAA CGCTACCAAG     1320

GACGTCAACC GCTGGACTTA CCTTGCCACC CAGCTCCATA ACCTCGTTCC ATTTTTGGGT     1380

ACTTTCCATG GTAGTGATCT TCTTTTCCAA TACTACGTGG ACCTTGGCCC ATCTTCTGCT     1440

TACCGCCGCT ACTTTATCTC GTTTGCCAAC CACCACGACC CCAACGTTGG CACCAACCTG     1500

AAACAGTGGG ATATGTACAC TGATGCAGGC AAGGAGATGC TTCAGATTCA TATGGTTGGT     1560

AACTCTATGA GAACTGACGA CTTTAGAATC GAGGGAATCT CGAACTTTGA GTCTGACGTT     1620

ACTCTCTTCG GTTAA                                                     1635
```

(2) INFORMATION FOR SEQ ID NO:6:

(i) SEQUENCE CHARACTERISTICS:
        (A) LENGTH: 1650 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:6:

```
ATGGAGCTCG CTCTTGCGCT CCTGCTCATT GCCTCGGTGG CTGCTGCCCC CACCGCCACG       60

CTCGCCAACG GCGACACCAT CACCGGTCTC AACGCCATCA TCAACGAGGC GTTCCTCGGC      120

ATTCCCTTTG CCGAGCCGCC GGTGGGCAAC CTCCGCTTCA AGGACCCCGT GCCGTACTCC      180

GGCTCGCTCG ATGGCCAGAA GTTCACGCTG TACGGCCCGC TGTGCATGCA GCAGAACCCC      240

GAGGGCACCT ACGAGGAGAA CCTCCCCAAG GCAGCGCTCG ACTTGGTGAT GCAGTCCAAG      300

GTGTTTGAGG CGGTGCTGCC GCTGAGCGAG GACTGTCTCA CCATCAACGT GGTGCGGCCG      360

CCGGGCACCA AGGCGGGTGC CAACCTCCCG GTGATGCTCT GGATCTTTGG CGGCGGGTTT      420

GAGGTGGGTG GCACCAGCAC CTTCCCTCCC GCCCAGATGA TCACCAAGAG CATTGCCATG      480

GGCAAGCCCA TCATCCACGT GAGCGTCAAC TACCGCGTGT CGTCGTGGGG GTTCTTGGCT      540

GGCGACGAGA TCAAGGCCGA GGGCAGTGCC AACGCCGGTT TGAAGGACCA GCGCTTGGGC      600

ATGCAGTGGG TGGCGGACAA CATTGCGGCG TTTGGCGGCG ACCCGACCAA GGTGACCATC      660

TTTGGCGAGC TGGCGGGCAG CATGTCGGTC ATGTGCCACA TTCTCTGGAA CGACGGCGAC      720

AACACGTACA AGGGCAAGCC GCTCTTCCGC GCGGGCATCA TGCAGCTGGG GGCCATGGTG      780

CCGCTGGACG CCGTGGACGG CATCTACGGC AACGAGATCT TTGACCTCTT GGCGTCGAAC      840

GCGGGCTGCG GCAGCGCCAG CGACAAGCTT GCGTGCTTGC GCGGTGTGCT GAGCGACACG      900

TTGGAGGACG CCACCAACAA CACCCCTGGG TTCTTGGCGT ACTCCTCGTT GCGGTTGCTG      960

TACCTCCCCC GGCCCGACGG CGTGAACATC ACCGACGACA TGTACGCCTT GGTGCGCGAG     1020

GGCAAGTATG CCAACATCCC TGTGATCATC GGCGACCAGA ACGACGAGGG CACCTTCTTT     1080

GGCACCCTGC TGTTGAACGT GACCACGGAT GCCCAGGCCC GCGAGTACTT CAAGCAGCTG     1140
```

```
TTTGTCCACG CCAGCGACGC GGAGATCGAC ACGTTGATGA CGGCGTACCC CGGCGACATC    1200

ACCCAGGGCC TGCCGTTCGA CACGGGTATT CTCAACGCCC TCACCCCGCA GTTCAAGAGA    1260

ATCCTGGCGG TGCTCGGCGA CCTTGGCTTT ACGCTTGCTC GTCGCTACTT CCTCAACCAC    1320

TACACCGGCG GCACCAAGTA CTCATTCCTC CTGAAGCAGC TCCTGGGCTT GCCGGTGCTC    1380

GGAACGTTCC ACTCCAACGA CATTGTCTTC CAGGACTACT TGTTGGGCAG CGGCTCGCTC    1440

ATCTACAACA ACGCGTTCAT TGCGTTTGCC ACGGACTTGG ACCCCAACAC CGCGGGGTTG    1500

TTGGTGAAGT GGCCCGAGTA CACCAGCAGC CTGCAGCTGG GCAACAACTT GATGATGATC    1560

AACGCCTTGG GCTTGTACAC CGGCAAGGAC AACTTCCGCA CCGCCGGCTA CGACGCGTTG    1620

TTCTCCAACC CGCCGCTGTT CTTTGTGTAA                                    1650
```